United States Patent
Ohnemus et al.

(10) Patent No.: US 8,706,530 B2
(45) Date of Patent: Apr. 22, 2014

(54) AUTOMATED HEALTH DATA ACQUISITION, PROCESSING AND COMMUNICATION SYSTEM

(75) Inventors: Peter Ohnemus, Küsnacht (CH); Andre Naef, Zurich (CH); Laurence Jacobs, Thalwil (CH); David Leason, Chappaqua, NY (US)

(73) Assignee: Dacadoo AG, Zurich (CH)

( * ) Notice: Subject to any disclaimer, the term of this patent is extended or adjusted under 35 U.S.C. 154(b) by 0 days.

(21) Appl. No.: 13/877,059

(22) PCT Filed: Sep. 29, 2011

(86) PCT No.: PCT/US2011/053971
§ 371 (c)(1),
(2), (4) Date: Apr. 23, 2013

(87) PCT Pub. No.: WO2012/050969
PCT Pub. Date: Apr. 19, 2012

(65) Prior Publication Data
US 2013/0211858 A1    Aug. 15, 2013

Related U.S. Application Data

(60) Provisional application No. 61/387,906, filed on Sep. 29, 2010, provisional application No. 61/495,247, filed on Jun. 9, 2011.

(51) Int. Cl.
G06Q 50/00    (2012.01)

(52) U.S. Cl.
USPC ............................................. 705/3; 705/319

(58) Field of Classification Search
USPC .................................................. 705/2–4, 319
See application file for complete search history.

(56) References Cited

U.S. PATENT DOCUMENTS

| | | |
|---|---|---|
| 6,514,199 B1 | 2/2003 | Alessandri |
| 6,616,578 B2 | 9/2003 | Alessandri |
| 7,628,730 B1 | 12/2009 | Watterson et al. |
| 8,075,450 B2 | 12/2011 | Fabbri et al. |
| 2002/0055418 A1 | 5/2002 | Pyles et al. |
| 2005/0076301 A1 | 4/2005 | Weinthal |
| 2005/0165618 A1 | 7/2005 | Nerenberg |
| 2007/0168230 A1 | 7/2007 | Roman |
| 2007/0276203 A1 | 11/2007 | Day |

(Continued)

FOREIGN PATENT DOCUMENTS

| | | |
|---|---|---|
| EP | 0709058 | 5/1996 |
| EP | 1087824 | 4/2001 |

(Continued)

Primary Examiner — Mark Holcomb
(74) Attorney, Agent, or Firm — Leason Ellis LLP

(57) ABSTRACT

A unique health score computation method is disclosed which masks underlying health statistics, yet provides a benchmark for a variety of applications. A system and method for collecting health related information, processing the information into a composite numerical value, and publishing the value is provided. The system includes a computer having a processor, memory, and code modules executing in the processor for implementation of the method. Information concerning a plurality of intrinsic and extrinsic parameters of a user is collected. Weighting factors are applied to the parameter in order control the relative affect each parameter has on the user's calculated numerical. The health score is computed using the processor by combining the weighted parameters in accordance with an algorithm. The numerical value is published to a designated group via a portal, while the underlying parameters remain private. In one implementation, the portal is an internet based information sharing forum.

22 Claims, 11 Drawing Sheets

(56) References Cited

U.S. PATENT DOCUMENTS

| | | |
|---|---|---|
| 2008/0089666 A1 | 4/2008 | Aman |
| 2009/0105047 A1 | 4/2009 | Guidi et al. |
| 2009/0156363 A1 | 6/2009 | Guidi et al. |
| 2009/0163774 A1 | 6/2009 | Thatha et al. |
| 2010/0004945 A1 | 1/2010 | Petratos et al. |
| 2010/0004947 A1 | 1/2010 | Nadeau et al. |
| 2010/0082362 A1 | 4/2010 | Salsbury et al. |
| 2012/0094649 A1 | 4/2012 | Porrati et al. |

FOREIGN PATENT DOCUMENTS

| | | |
|---|---|---|
| EP | 1259153 | 11/2002 |
| EP | 1400284 | 3/2004 |
| EP | 2025368 | 2/2009 |
| WO | WO 2007/112034 | 10/2007 |
| WO | WO 2009/026156 | 2/2009 |

Fig. 3B

① You are viewing: Ken Purcell's Desktop                                    Logout  English (UK) ▷

⊕ 669

GENERAL
QUENTIQ Health Score®
Lifestyle
Medical History

FITNESS
Walking
Running
Cycling
Mountain Biking
Inline Skating
Downhill Skiing
Cross Country Skiing
Generic Workout

HOME MONITORING
Weight
Body Dimensions
Body Mass Index
Blood Pressure

LAB MONITORING
Lipids
Glucose

| Home | Profile | Achievements | Challenges | Journal | Forums |

QUENTIQ Health Score®  Journal of Andre Naef

Sub Scores | Chart | Friends | Table

30 Days ▷

| Component | Score |
|---|---|
| QUENTIQ Health Score® | 669 |
| Health Reservoir Score | 676 |
| Health Pool | 202.7 |
| Bonus Pool | 6.7 |
| Daily Decay | 4.2 |
| Metric Health Score | 776 |
| BMI | 440 |
| Total Cholesterol | 279 |
| High-density Lipoproteins | 662 |
| Low-density Lipoproteins | 620 |
| Serum Triglycerides | 715 |
| Fasting Blood Glucose | 659 |
| Systolic Blood Pressure | 711 |
| General Health Score | 633 |

Alerts

Fig. 3C

You are viewing: Ken Purcell's Desktop

Logout [English (UK) ▷]

(669)

GENERAL
QUENTIQ Health Score®
Lifestyle
Medical History

FITNESS
Walking
Running
Cycling
Mountain Biking
Inline Skating
Downhill Skiing
Cross Country Skiing
Generic Workout

HOME MONITORING
Weight
Body Dimensions
Body Mass Index
Blood Pressure

LAB MONITORING
Lipids
Glucose

[ Home | Profile | Achievements | Challenges | Journal | Forums ]

QUENTIQ Health Score ®  Journal of Andre Naef         [30 Days ▷]

Sub Scores | Chart | Friends | Table                          ← Previous

| Member | Health Score | Δ 1 Day | Δ 7 Day | Reason | 7 Day Δ Prediction |
|---|---|---|---|---|---|
| Herbert Schnider | 874 | -1 | -5 | No Activity | -6 |
| Gabriela Keller | 867 | -1 | -5 | No Activity | -6 |
| Dominik Stucki | 829 | -1 | -5 | No Activity | -6 |
| Kasper Weis | 820 | -1 | -5 | No Activity | -6 |
| Manuel Heuer | 797 | -1 | -5 | No Activity | -6 |
| Laurence Jacobs | 794 | -1 | -5 | No Activity | -6 |
| Dominic Small | 747 | -1 | -5 | No Activity | -6 |
| Markus Schrodel | 732 | -1 | -5 | No Activity | -6 |
| Jurg Gabathuler | 687 | -1 | -5 | No Activity | -6 |
| Irene Janssen | 670 | -4 | -8 | No Activity/Poor Diet | -7 |
| Andre Naef | 669 | +2 | +7 | Moderate Activity | +5 |
| Helle Ohnemus | 668 | -1 | -1 | Low Activity/Good Diet | -1 |
| Katrin Luethi | 658 | -1 | -5 | No Activity | -6 |
| isabella ohnemus | 658 | -1 | -5 | No Activity | -6 |
| Torbjoern Winther | 652 | -1 | -5 | No Activity | -6 | http://www.quentiq.com/journal/healthscore/friends:to=[0]to1&interval=30

Fig. 3D

AUTOMATED HEALTH DATA ACQUISITION, PROCESSING AND COMMUNICATION SYSTEM

CROSS-REFERENCE TO RELATED APPLICATIONS

This application claims the benefit of U.S. Patent Application Ser. No. 61/387,906, filed Sep. 29, 2010, and U.S. Patent Application Ser. No. 61/495,247, filed Jun. 9, 2011, which are hereby incorporated by reference in their entireties.

FIELD OF THE INVENTION

The present invention concerns a computer implemented system for the acquisition of medical data and its processing for diagnostic, benchmarking, analytics and redistribution purposes. More particularly, the invention concerns a computer implemented system and method for acquisition, diagnosis, benchmarking, analytics and/or redistribution of medical data.

BACKGROUND OF THE INVENTION

Despite advances in many areas of technology, there are still barriers to assessing the relative health of a person in a rapid, cost effective, and timely manner. With the increase in health care costs and prevalence of diseases related to unhealthy lifestyles such as diabetes and heart disease, it is important to assess the relative health of individuals, and this has not been adequately addressed. In many areas of the world, access to doctors is limited. Even in the developed world, a doctor's time is considered a precious commodity and there are often long waiting lists and doctor-to-specialist referral systems have to be navigated before being seen. In more developed countries the ratio of doctors to the population may be on the order of 1:1,000 persons, while in less developed countries the ratio may be 1:100,000. There are also cost barriers to having access to a doctor because an appointment with a doctor can be very expensive, especially if an individual does not have any health insurance or lacks sufficient coverage. Accordingly, it can be very difficult to gain access to medical professionals in order to receive information about one's health.

Even if an individual had access to his or her health information, the mechanisms for conveying that information to others is lacking or non-existent. Privacy laws restrict the type of information that can be shared and the manner in which it can be shared. Privacy laws relating to health information are particularly strict in regard to the information that can be shared. This is to protect a person from disclosure of sensitive information. Accordingly, the sharing of health related information is generally discouraged. It is also difficult to share health related information with friends and family. Often health information is only verbally conveyed by a doctor to a patient, or the patient will only receive paper copies of lab test results. Systems are lacking for easily sharing such information with others, especially with large groups of persons located in geographically remote locations.

Prior art systems that provide a limited type of numerical score which is related to a person's health have been disclosed. For example, U.S. Patent Publication No. 2009/0105550 to Rothman et al. discloses a system and method for providing a health score for a patient. However, this disclosure is primarily directed to calculating a health score of a patient in a hospital, post surgery, and the health score is based on medical data measured from the patient (e.g., blood pressure, temperature, respiration, etc.). This method fails to take into account the extrinsic activities of the patient, such as the daily physical exercise activities of the patient. U.S. Patent Publication No. 2005/0228692 to Hodgdon discloses a system that calculates a health score based on measured medical data and can include a self assessment survey, which can include surveying a participant's exercise habits. However, this only takes into account a person's purported habits, not the actual exercise activity that a person engages in each day. Accordingly, the score is static and does not change in relation to actual activity performed.

Such disclosed systems are primarily directed to medical practitioners for addressing issues in continuity of care and require input from practitioners in order to produce and maintain scores. Clearly, while the attention of a medical practitioner is needed in emergency and critical care situations, cost and resource factors mean that such systems are usable only in such situations and such systems do not address the general issues discussed above. Additionally, the score is only relevant to the particular instant in time at which it was last updated by the medical practitioner.

SUMMARY OF THE INVENTION

According to an aspect of the present invention, there is provided a computer implemented method for processing private health related data into a masked numerical score suitable for publishing. The method comprises receiving data into a memory on a plurality of intrinsic medical parameters and extrinsic physical activity parameters of a user. The received data and weighting factors are stored in the memory. The received data is processed by executing code in a processor that configures the processor to apply the weighting factors to the intrinsic medical parameters and the extrinsic physical activity parameters. The weighting factors for at least the extrinsic physical activity parameters include a decay component arranged to reduce the relative weight of the extrinsic physical activity parameters for a physical activity in dependence on at least one factor associated with the user. The processed data concerning the intrinsic medical parameters and the extrinsic physical activity parameters are transformed by further code executing in the processor into a masked composite numerical value in which the code is operative to combine the weighted parameters in accordance with an algorithm. The masked composite numerical value is automatically published to a designated group via a portal (such as a social web site) using code executing in the processor and free of any human intervention. Meanwhile, the collected information concerning the intrinsic medical parameters and the extrinsic physical activity parameters is maintained private.

According to a further aspect of such a method as can be implemented in a particular embodiment thereof, the factor associated with the user can be an age or an age range of the user such that the decay component reduces the relative weight of the extrinsic physical activity parameters for a first user of a first age or age range differently than a second user of a second age or age range.

According to still another aspect of such a method as can be implemented in a particular embodiment thereof, the published masked composite numerical value can comprise an average of a group of users to arrive at a group composite numerical value determination using further code executing in the processor.

According to an additional aspect of the present invention, there is provided a computer implemented health monitoring system which comprises a communication unit operable to receive data on a plurality of intrinsic medical parameters and extrinsic physical activity parameters of a user. A memory is arranged to store the received data and to store weighting factors. Also, a processor is arranged to process the received data by executing code that configures the processor to apply the weighting factors to the intrinsic medical parameters and the extrinsic physical activity parameters. The weighting factors for at least the extrinsic physical activity parameters include a decay component arranged to reduce the relative weight of the physical activity parameters for a physical activity in dependence on at least one factor associated with the user. The processor is further arranged to execute code to transform the processed data concerning the intrinsic medical parameters and the extrinsic physical activity parameters into a masked composite numerical value using the processor by combining the weighted parameters in accordance with an algorithm. A portal is arranged to publish the masked composite numerical value to a designated group while maintaining the collected information concerning the intrinsic medical parameters and the extrinsic physical activity parameters private.

Such a system can preferably be configured so that the factor associated with the user can be an age or an age range of the user such that the decay component reduces the relative weight of the extrinsic physical activity parameters for a first user of a first age or age range differently than a second user of a second age or age range.

An embodiment in accordance with further aspects of the invention can comprise a system that communicates either the processed data or the masked composite numerical value to an exercise machine. The machine works in conjunction with the system through programming thereat to automatically establish an exercise program on the basis of the communicated data or the masked composite numerical value. Preferably, the system so-configured receives from the exercise machine into its memory activity information for inclusion among the extrinsic physical activity parameters.

Embodiments of the present invention seek to combine data from multiple medical and non-medical sources in a system and method that produce a normalized score for a person that takes into account available medical, physical activity and optionally lifestyle data (such as diet) in an arrangement that can be operated and updated in substantially real-time and does not need frequent access to a medical practitioner. The score and trends associated with it can be used for various purposes including triggering alerts as to possible medical issues or repercussions, providing user feedback, automated motivation and/or goal setting, training scheduling, automated referrals for medical analysis. Among the alerts that can be generated are alerts that are triggered based on monitoring of a composite numerical value of a health score that is computed, the computed value of which can cause a feedback communication to be sent to the user (e.g., within the system portal or by email, SMS, etc.), as a result of code executing in a processor and without human intervention, if the monitoring detects a change in the user's score such as due to decay in value by operation of the algorithm, or reduction in value due to eating habits, or in fulfillment of goals input into the system by the user or by a group the user has associated with, or as part of a non-user-specific goal program that the system can have to motivate wellness (e.g., good exercise or eating habits). Embodiments of the present invention apply a weighting factor to the respective physical activity and/or lifestyle data such that recent events have a greater impact on the score than those that occurred further in the past.

In the described embodiments, a unique health score computation method is disclosed which masks underlying health statistics, yet provides a benchmark for a variety of applications. In one embodiment, a method for collecting and presenting health related data is provided. The method includes collecting information concerning a plurality of intrinsic medical parameters and extrinsic physical activity parameters of a user. The collected information is stored in a memory and weighting factors are stored in the memory. The collected information is processed by executing code in a processor that configures the processor to apply the weighting factors to the intrinsic medical parameters and extrinsic physical activity parameters. The collected information concerning the intrinsic medical parameters and extrinsic physical activity parameters is transformed into a masked composite numerical value using the processor by combining the weighted parameters in accordance with a predetermined algorithm. The masked composite numerical value is published to a designated group via a portal while maintaining the collected information concerning the intrinsic medical parameters and extrinsic physical activity parameters private.

Preferred embodiments of the present invention seek to provide a normalized rating system that can provide an assessment of the relative health of an individual that can be used as the basis of a fair comparison to other individuals having different ages, sex, medical status or lifestyles.

Various features, aspects and advantages of the invention can be appreciated from the following Description of Certain Embodiments of the Invention and the accompanying Drawing Figures.

DESCRIPTION OF THE DRAWING FIGURES

FIGS. 3a-3e are screen shots of a user interface according to one embodiment of the invention;

DETAILED DESCRIPTION OF CERTAIN EMBODIMENTS OF THE INVENTION

Figure 1:
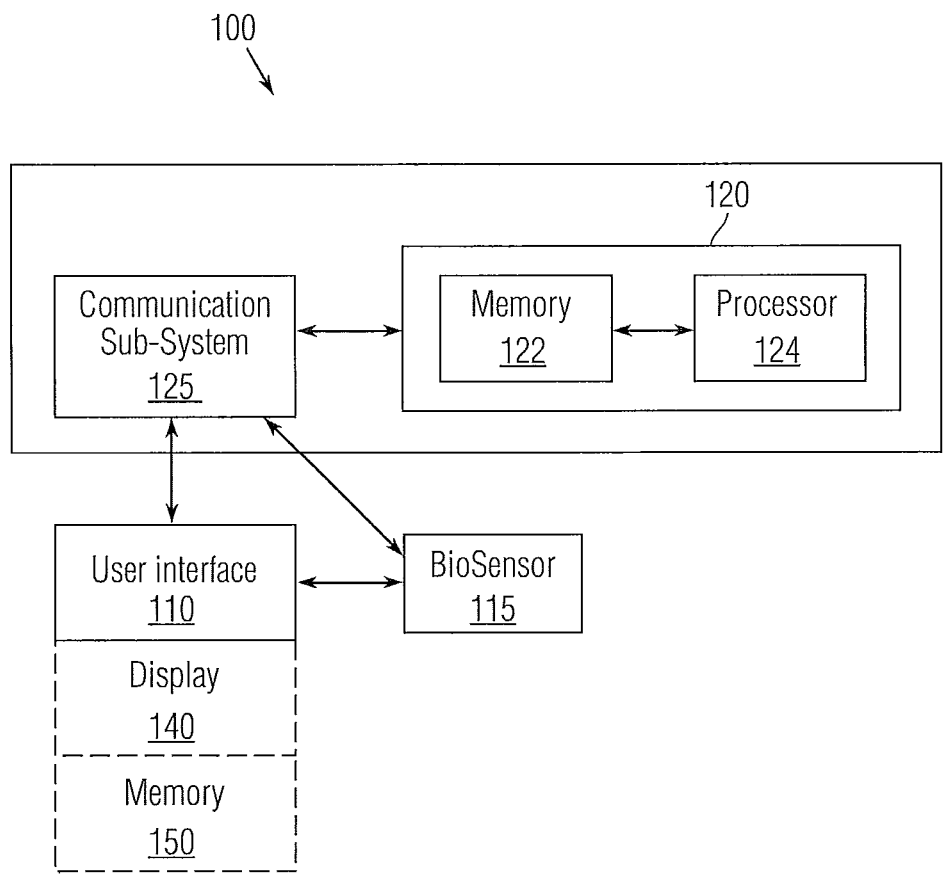
FIG. 1 is a schematic block diagram of a local health information collection and communication system according to a first implementation of the invention.

By way of overview and introduction, the present invention is described in detail in connection with a distributed system in which data acquisition, data storage, and data processing are used to produce a numerical score as a basis for assessing the relative health of a user.

In one implementation, a system 100 includes a computer-based application for the collection of health related parameters of a user and a user interface 110 for the display of data. The computer-based application is implemented via a microcontroller 120 that includes a processor 124, a memory 122 and code executing therein so as to configure the processor to perform the functionality described herein. The memory is for storing data and instructions suitable for controlling the operation of the processor. An implementation of memory can include, by way of example and not limitation, a random access memory (RAM), a hard drive, or a read only memory (ROM). One of the components stored in the memory is a program. The program includes instructions that cause the processor to execute steps that implement the methods described herein. The program can be implemented as a single module or as a plurality of modules that operate in cooperation with one another. The program is contemplated as representing a software component that can be used in connection with an embodiment of the invention.

A communication subsystem 125 is provided for communicating information from the microprocessor 120 to the user interface 110, such as an external device (e.g., handheld unit or a computer that is connected over a network to the communication subsystem 125). Information can be communicated by the communication subsystem 125 in a variety of ways including Bluetooth, WiFi, WiMax, RF transmission, and so on. A number of different network topologies can be utilized in a conventional manner, such as wired, optical, 3G, 4G networks, and so on.

The communication subsystem can be part of a communicative electronic device including, by way of example, a smart phone or cellular telephone, a personal digital assistant (PDA), netbook, laptop computer, and so on. For instance, the communication subsystem 125 can be directly connected through a device such as a smartphone such as an iPhone, Google Android Phone, BlackBerry, Microsoft Windows Mobile enabled phone, and so on, or a device such as a heart rate or blood pressure monitor (such as those manufactured by Withings SAS), weight measurement scales (such as those manufactured by Withings SAS), exercise equipment or the like. In each instance, the devices each comprise or interface with a module or unit for communication with the subsystem 125 to allow information and control signals to flow between the subsystem 125 and the external user interface device 110. In short, the communication sub-system can cooperate with a conventional communicative device, or can be part of a device that is dedicated to the purpose of communicating information processed by the microcontroller 120.

When a communicative electronic device such as the types noted above are used as an external user interface device 110, the display, processor, and memory of such devices can be used to process the health related information in order to provide a numerical assessment. Otherwise, the system 100 can include a display 140 and a memory 150 that are associated with the external device and used to support data communication in real-time or otherwise. More generally, the system 100 includes a user interface which can be implemented, in part, by software modules executing in the processor of the microcontroller 120 or under control of the external device 130. In part, the user interface can also include an output device such as a display (e.g., the display 140).

Biosensors 115 can be used to directly collect health information about a user and report that information. The biosensor can be placed in contact with the user's body to measure vital signs or other health related information from the user. For example, the biosensor can be a pulse meter that is worn by the user in contact with the user's body so that the pulse of the user can be sensed, a heart rate monitor, an electrocardiogram device, a pedometer, a blood glucose monitor or one of many other devices or systems. The biosensor can include a communication module (e.g., communication subsystem 125) so that the biosensor can communicate, either wired or wirelessly, the sensed data. The biosensor can communicate the sensed data to the user interface device, which in turn communicates that information to the microcontroller. Optionally, the biosensor can directly communicate the sensed the data to the microprocessor. The use of biosensors provides a degree of reliability in the data reported because it eliminates user error associated with manually, self-reported data.

Figure 1A:
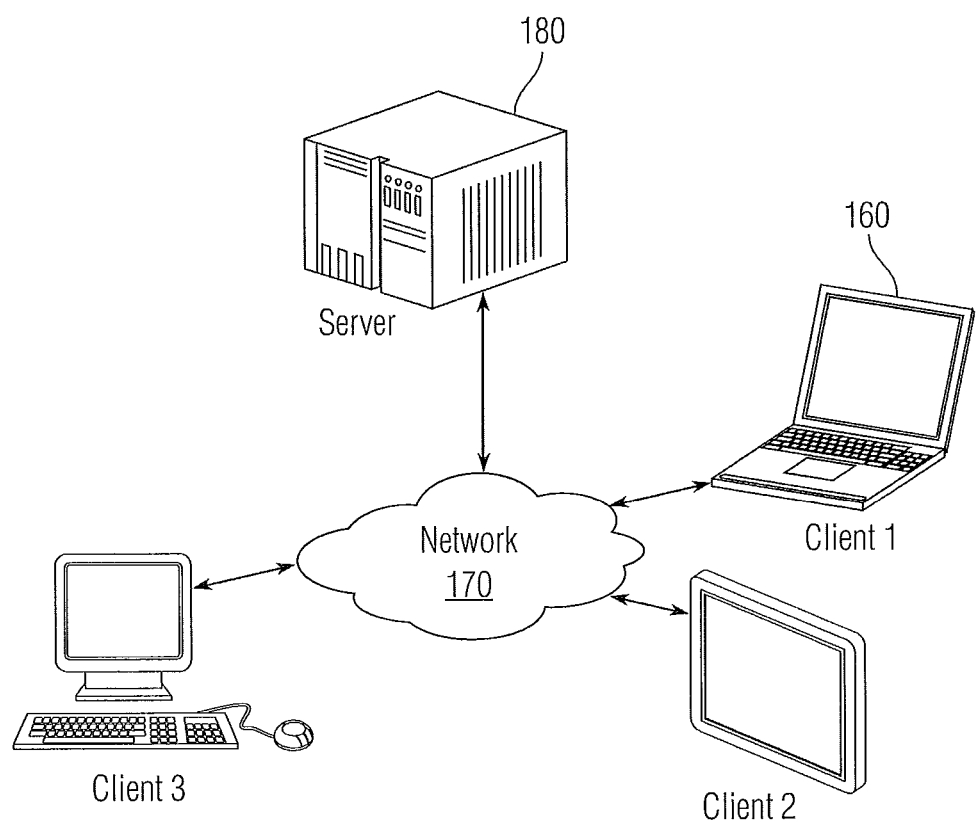
FIG. 1A is a network diagram according to another implementation of the invention.

Alternatively or in addition, the user can self-report his or her health related information by manually inputting the data. Thus, in another implementation, as shown in FIG. 1A, health related data of a person is entered directly into a computer 160 and provided across a network 170 to a server computer 180. (All computers described herein have at least one processor and a memory.)

Regardless of the implementation, the system provides a means for assigning a numerical value that represents the relative health of an individual. The numerical value is described herein as a "health score" and can be used to assess to the individual's health based on health related information collected from a user. The health score is calculated based on the collected health information using an algorithm. The user or the communication subsystem 125 provides the system the health related information concerning a number of health parameters. Predetermined weighting factors are used to assign a relative value of each of the parameters that are used to calculate the health score. The user's health score is then calculated by combining the weighted parameters in accordance with an algorithm. For example, the parameters can be a person's blood glucose level and body weight. A weighting factor "a" is applied to the blood glucose data and a weight factor "b" can be applied to the body weight data. If the blood glucose data is a more important factor in determining a person's health than body weight, then the weighting factor "a" will be larger than weighting factor "b" so that the blood glucose data has a larger impact on the calculated health score (e.g., Healthscore=Glucose*a+(Weight/100)*b). In certain implementations, the weighting factor is a non-unity value (e.g., greater or less than one, but not one). Fewer or additional factors can be included in the calculation of the health score, and an offset value can be included that is added or subtracted or which modifies the entire calculation, in certain implementations such as to account for age or gender as two possible reasons; however, the foregoing is intended as a non-limiting example of how to calculate a health score. Other parameters that can be measured and included in the calculation include blood pressure measurements, height, body mass index, fat mass, medical conditions such as diabetes, ventricular hypertrophy, hypertension, irregular heartbeat and fasting glucose values. Where absent, a parameter can be omitted from the calculation or it can be estimated from other parameters and/or values obtained from a sample group of individuals having similar parameters.

In addition to intrinsic medical parameters, physical activity of a user is also taken into account when calculating his or her health score. Physical activity can be monitored via an appropriate sensor dependent on the activity. Sensors can include a GPS unit, an altimeter, a depth meter, a pedometer, a cadence sensor, a velocity sensor, a heart rate monitor or the like. In the case of gym-based activities, computerized exercise equipment can be configured to provide data directly on the program completed by the user (for example, a so-called elliptical/cross-trainer can provide far better data on the workout than a user's pedometer etc). Although automated capture of parameters concerning a user's physical activity is preferred, a user interface for manual activity entry is also provided. In this regard, an exercise machine such as a treadmill, elliptical, stationary bike or weight lifting machine with a rack of weights or bands can be provided with a communications interface to communicate with the system described herein to provide extrinsic physical activity parameters to the system and to receive and further include a processor configured to process data from the system so as to automatically adjust an exercise program at the exercise machine to meet a goal, challenge, or other objective for that user. Lifestyle data such as diet, smoking, alcohol consumed and the like can also be collected and used in calculating the health score. In one embodiment, a barcode or RFID scanner can be used by a user to capture data on consumed foodstuffs that is then translated at a remote system, such as the server 180 or a website in communication with the server 180, into parameters such as daily calorie, fat and salt intake. In part, the system relies on such data being provided by the user while other data can be obtained through data network connections once permissions and connectivity rights are in place.

Physical activity and lifestyle data is tracked over time and a decay algorithm is applied when calculating its effect on the health score, as is discussed in more detail below. As such, physical activity far in the past has a reduced positive effect on the health score. Preferably, the weighting factors used in the algorithm for the computation of the health score are adjusted over time in accordance with a decay component which is arranged to reduce the relative weight of the parameters that are used in the calculation. The decay component can itself comprise a weighting value, but can also comprise an equation that takes into account at least one factor associated specifically with the user, such as the user's weight or weight range, age or age range, any medical conditions known to the system, and any of the other parameters that may be known to the system, or a curve that is configured in view of these factors so that a value can be read from the curve as a function of the values along the axes for that user. In this way, the decay component can reduce the relative weight of the parameters used in the health score calculation for a first user differently than for another user, such as when the first user has a first age or age range and the second user has a second age or age range.

A central system, preferably a database and website that can be hosted, for example, by the server 180, maintains data on each user and his or her health score and associated parameters and their trends over time. The data can be maintained in such a way that sensitive data is stored independent of human identities, as understood in the art.

The calculated health score for each user is then processed in dependence on a system, group or user profile at the central system. Depending on the profile settings, the health score and trends associated can cause various automated actions. For example, it can cause: triggering of an automated alert; providing user feedback such as a daily email update; triggering the communication of automated motivation, warnings and/or goal setting selected to alleviate a perceived issue; adjustment of a training programme; or automated referral for medical analysis.

The user's health score is also provided to a designated group of recipients via a communication portal. The group of recipients can comprise selected, other, users of the system (e.g., friends and family) so that the health scores of the selected, other users can be compared against the health score of still others. In alternative arrangements, all users can see other user's scores, or the group of recipients can be defined as a specific health insurance provider so that price quotes can be provided to insure the individual. Other possibilities are within the scope the invention.

Figure 2:
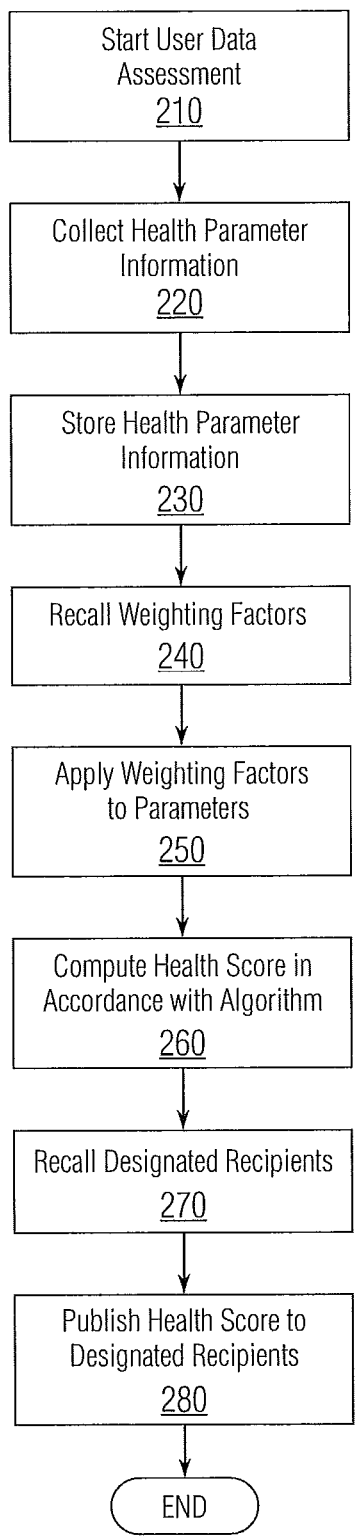
FIG. 2 is a schematic flow diagram according to one embodiment of the invention.

Referring now to FIG. 2, a schematic flow diagram according to one embodiment of the invention is described in support of an assessment of a person (e.g., a patient or user) to provide a health score. At step 210, the user initiates the process for the collection, processing, and publishing of health related data. For example, a person using a mobile electronic device (e.g. a smart phone or portable computing device) selects the software application, which starts the program running on the device processor, or the user can access an Internet based web page in which code is executed on a remote processor and served to the user's local device. An identification module prompts the user to identify himself and authenticate his identity. This can be accomplished by prompting the user to enter a user name and password, or by other means, such as a fingerprint reader, keyfob, encryption or other mechanism to ensure that identity of the user. Alternatively, if the user is accessing the system via a personal electronic device, identification data can be stored in the local device memory and automatically accessed in order to automatically confirm the identity of the user.

At step 220, a data collection module executing on the processor can prompt the user to provide health related data corresponding to a number of parameters. In one implementation, one or more the parameters are provided automatically by the communication subsystem 125. The parameters can include the user's body weight, height, age and fitness activity information. Such measurable medical parameters are intrinsic parameters of the user. The user's body weight and height provide information about the user's current state of health. The fitness activity information corresponds to the amount of exercise the user engages in. This information is an example of a physically activity parameter that is an extrinsic parameter of the user. For example, the user can enter information about his or her daily fitness activities, such as the amount of time the user engaged in physical activity and the type of physical activity. If the user went to the gym and exercised on a bicycle for thirty minutes, for example, that information is entered into the system. The user's fitness activity information provides information about the actions that are being taken by the user in order to improve his or her fitness.

A user's body weight, height, age and fitness activity information are just some of the parameters for which information can be collected. The system can collect and process a multitude of other parameters that can be indicative of a user's health. For example, parameters can include blood glucose levels, blood pressure, blood chemistry data (e.g., hormone levels, essential vitamin and mineral levels, etc.), cholesterol levels, immunization data, pulse, blood oxygen content, information concerning food consumed (e.g., calorie, fat, fiber, sodium content), body temperature, which are just some of a few possible, non-limiting examples of parameters that can be collected. Various other parameters that are indicative of a person's health that can be reliably measured could be used to calculate a person's health score.

The collected health parameter information is stored in a memory at step 230. At step 240, a weighting module recalls weighting factors from the memory. The weighting factors can be multiplication coefficients that are used to increase or decrease the relative value of each health parameters. A weighting factor is assigned to each health parameter as shown in the formulas herein. The weighting factors are used to control the relative values of the health parameters. Some health parameters are more important than others in the calculation of the users health score. Accordingly, weighting factors are applied to the health parameters increase or decrease the relative affect each factor has in the calculation of the user's health score. For example, a user's current body weight can be more important than the amount of fitness activity the user engages in. In this example, the body weight parameter would be weighted more heavily by assigning a larger weighting factor to this parameter. At step 205, the weighting module applies the recalled weighting factors to the collected health parameter values to provide weighted health parameter values. The weighting factor can be zero in which case a particular parameter has no impact on the health score. The weighting factor can be a negative value for use in some algorithms.

After the parameters have been weighted, the user's health score is computed at step 260 via a scoring module operating in the processor. The scoring module combines the weighted parameters according to an algorithm. In one implementation, the health score is the average of the user's body mass index (BMI) health score and the user's fitness health score minus two times the number of years a person is younger than 95. The algorithm formula for this example is reproduced below:

$$\text{Health Score}=((\text{BMI Healthscore}+\text{Fitness Healthscore})/2)-2*(95-\text{Age}).$$

The user's BMI Healthscore is a value between 0 and 1000. The BMI Healthscore is based on the user's BMI, which is calculated based on the user's weight and height, and how much the user's BMI deviates from what is considered a healthy BMI. A chart or formula can be used to normalize the user's BMI information so that dissimilar information can be combined. A target BMI value is selected which is assigned a maximum point value (e.g. 1000). The more the user's BMI deviates from the target value the fewer points are awarded. The user's Fitness Healthscore is based on the physical activity or exercise of a person. In one embodiment, it is the sum of the number of fitness hours (i.e., the amount of time the user engaged in fitness activities) in the past 365 days where each hour is linearly aged over that time so that less recent activity is valued less. The resulting sum is multiplied by two and is capped at 1000. This normalized the fitness information so that it can be combined to arrive at the health score. A target daily average of fitness activity is selected and is awarded the maximum amount of points (e.g. 1000). The user is awarded fewer points based on how much less exercise that engage in compared to the target.

In another implementation, the health score is determined from a number of sub-scores that are maintained in parallel beyond the BMI health score and the fitness health score. Likewise, the health score can be determined using similar information in a combinative algorithm as discussed above using different or no age adjustments.

Figure 3A:
Figure 3B:
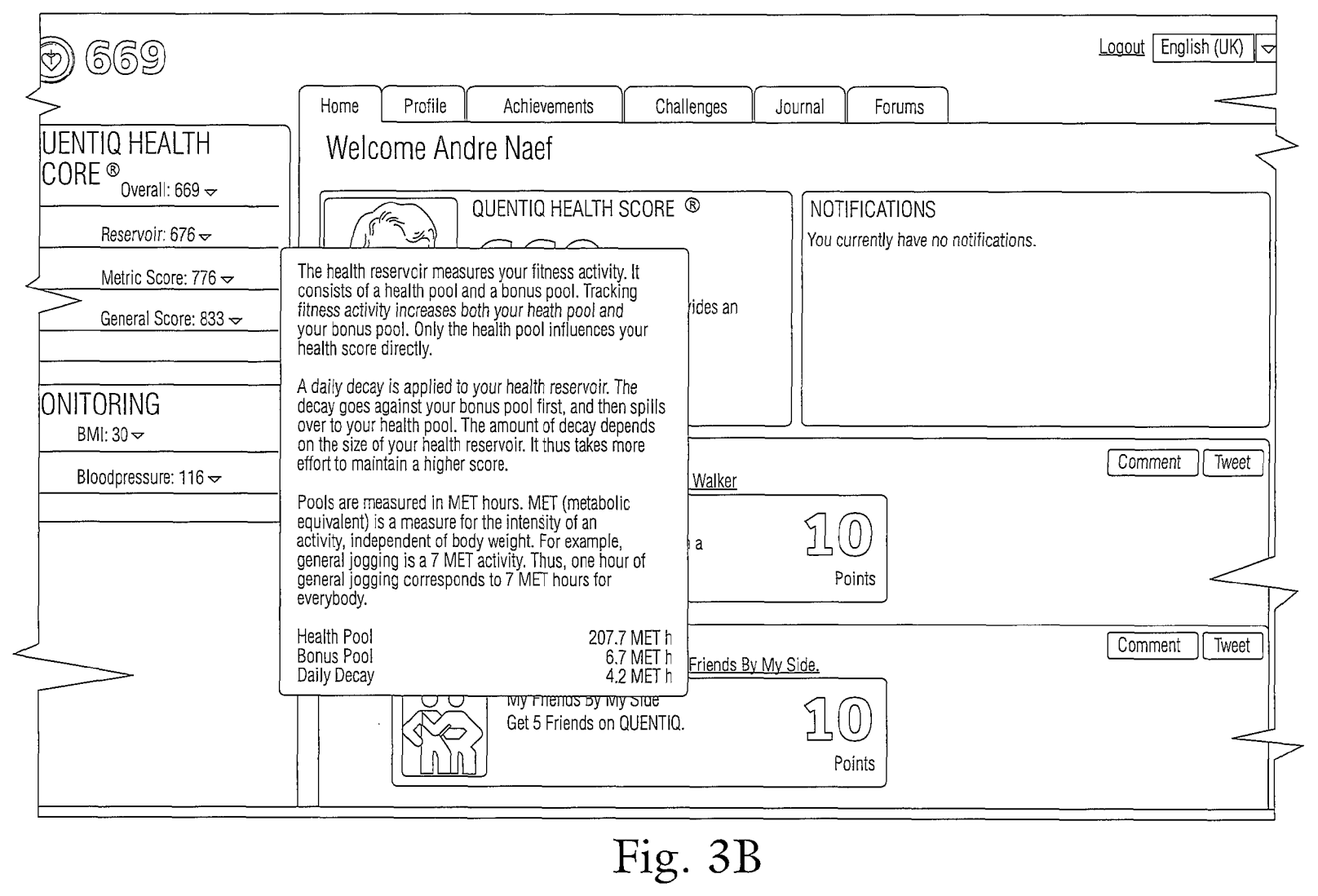

Intrinsic medical parameters are processed to determine a base health score. Extrinsic parameters such as those from physical exercise are processed to determine a value that is allocated to a health pool and a bonus pool. The value, preferably expressed in MET hours, associated with a physical activity is added to both the health pool and the bonus pool. A daily decay factor is applied to the bonus pool. Any excess decay that cannot be accommodated by the bonus pool is then deducted from the health pool. The amount of decay is determined dependent on the size of the health pool and bonus pool such that a greater effort is required to maintain a high health and bonus pool. The health pool value is processed in combination with the score from the intrinsic medical parameters in order to calculate the overall health score value. This can be on a similar basis to the earlier described implementation or it can include different parameters and weighting factors. In one embodiment, the health pool value is a logarithm or other statistical function is applied to age the respective values over time such that only the most recent activity is counted as being fully effective to the health/bonus pool. An example user interface showing the health score, the health reservoir and selected other measured parameters (as it will be appreciated that many simply combine to make up the scores) is shown in FIGS. 3*a* and 3*b*. Various sub-scores and their trends are recorded, as is shown in FIG. 3*c*.

As will be appreciated, MET hours are kcal expended divided by kilograms of body weight, i.e. 100 kcal expended by a person of 50 kg is 2 MET h. This is "normalized energy", making the system fair for persons of all weights. With this method, pools can be the same size for each per person as energy is normalized for the person based on his or her body weight.

In one implementation, each person is assigned a health pool having a capacity of 300 MET h and a bonus pool having a capacity of 60 MET h.

When someone performs activity A, the pools are updated as follows:

$$H=\min(H+A*\text{alpha},300)$$

$$B=\min(B+A*(1-\text{alpha}),60)$$

Where H is the health pool score, B is the bonus pool score, A is the MET h value for the activity and alpha is a system wide contestant (selected between 0 and 1) that determines the proportion in which the activity contributes to the respective pools.

The activity is split between the health pool and the bonus pool. Any excess MET h activity going over the cap of any pool is discarded. A daily decay value D is applied to the pools as follows:

$$D=f(H,B)$$

$$B=B-D$$

If $B<0$:

$$D=D+B$$

$$B=0$$

If $D<0$:

$$D=0$$

The decay is fully applied to the bonus pool, and if the bonus pool is empty, the remainder is applied to the health pool. In this embodiment, no pool ever goes below zero.

Figure 3E:
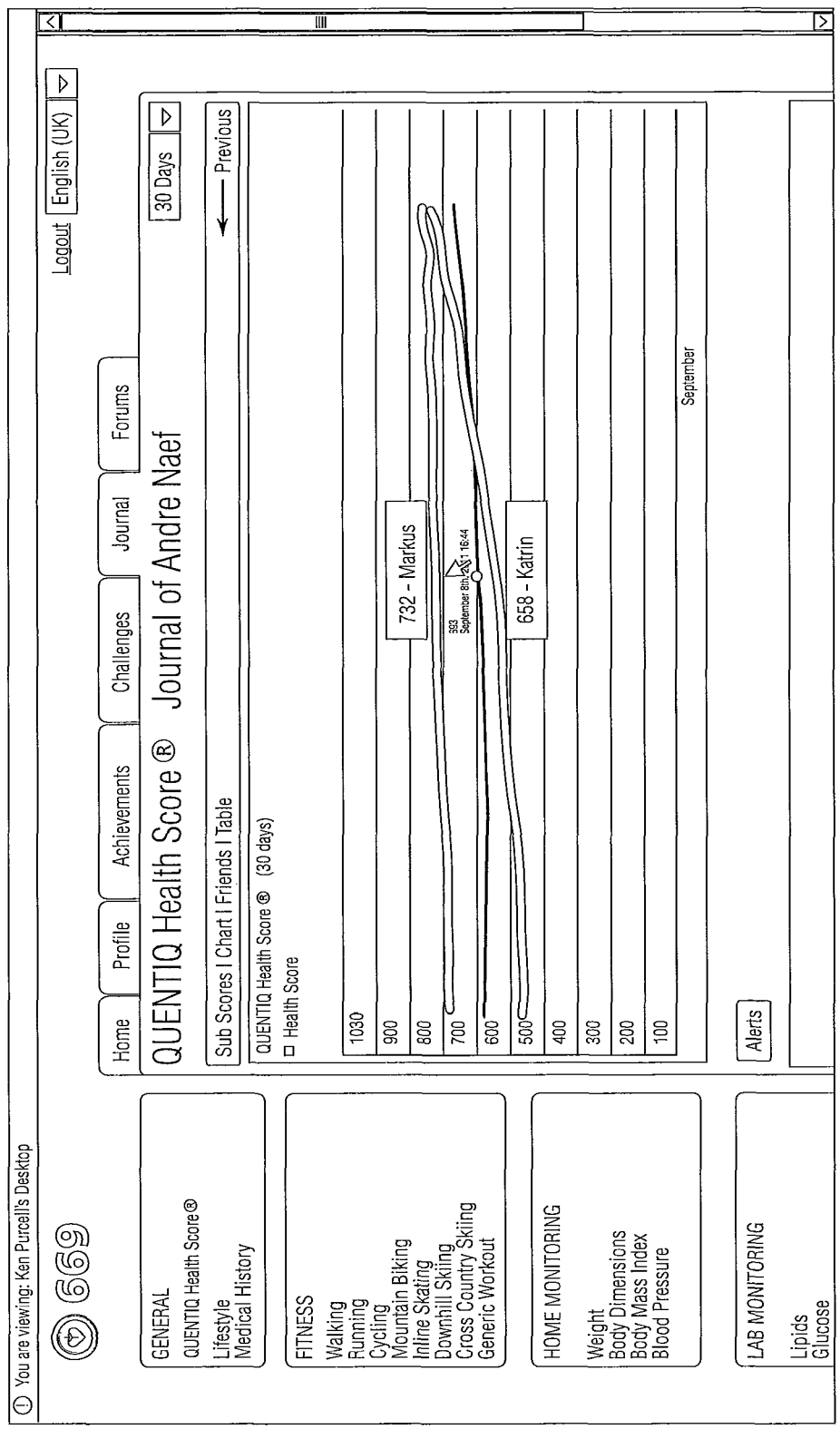
Figure 3F:
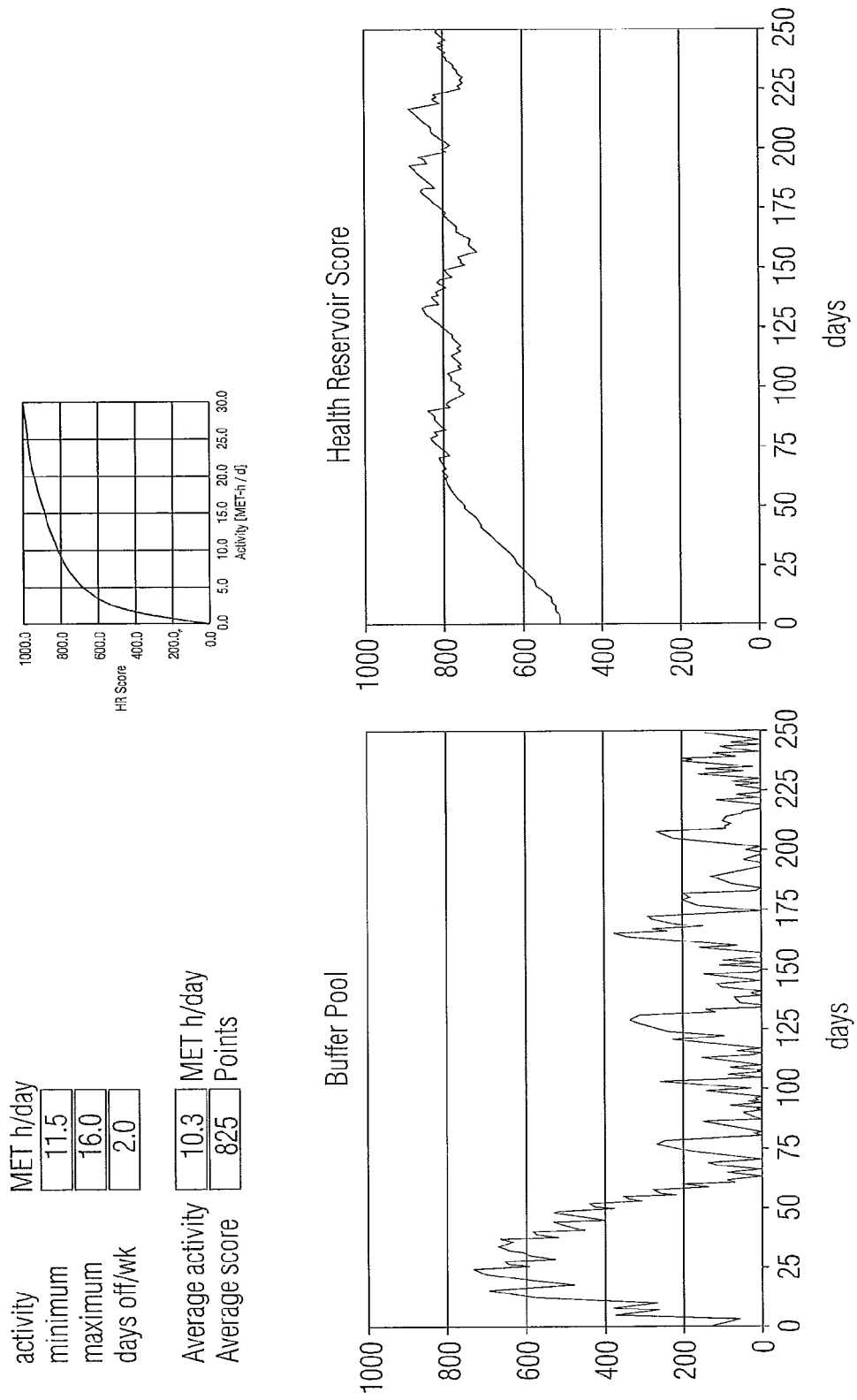
FIG. 3f is an illustration of progressions over time of parameters used to determine the health score in one embodiment of the invention.

The system finds its equilibrium where A equals f(H, B), i.e. where the average daily activity matches the average daily decay. The function f(H, B) is highly non-linear with regard to H and B. In essence, it takes sub-linearly less effort to maintain a small pool, and super-linearly more effort to maintain a large pool. This is to make sure that the average person can maintain a, say, half-full health pool (150, corresponding to a score of 500), whereas it takes a massively higher effort (typically only delivered by a professional endurance athlete) to maintain a full health pool (300, corresponding to a score of 1000). FIG. 3*f* shows a simulation of the buffer pool and health reservoir score over time assuming activity varying between 11.5 and 16 MET h per day and 2 days off per week. A perfect health reservoir score of 1000 would require 30 MET h activity per day, as can be seen from the curve in the top right corner of FIG. 3*f*

Preferably, the health score is based on a weighted combination of health factor(s) and the exercise record of the person over time. The health factors can be updated regularly by the user. For example, the user can provide health related information after every event that is tracked and processed by the system. The user can update after a meal, after exercising, after weighing himself, etc. In the case of recordal of an activity/event by a sensor, portable device or the like, the captured/calculated parameters can be automatically uploaded and used to produce a revised health score. For example, feedback could be provided showing the effect of exercise while a user is running, working out on exercise equipment etc. In selected embodiments, feedback can be provided to an administrator such as a gym staff member where it is determined that a user is exceeding a predetermined threshold (which due to knowledge of their health can be varied respective to their health score or other recorded data). Accordingly, the health related data can be updated in a near real-time manner.

The user can also update the information twice daily, once daily, or at other periodic times. Moreover, the health score can be based on an average of the information over time. Fitness activity, for example, can be averaged over a period of time (e.g. over a week, month, or year). Averaging data over time will reduce the impact to the health score caused by fluctuations in data. Periods in which the data was uncharacteristically high (e.g., the person was engaging large amount of fitness activity over a short period of time) or uncharacteristically low (e.g., person engaged in no fitness activity for a week due to an illness) does not dramatically affect the health score with averaging over time. The health related information can be stored in the memory or in a database accessible by the processor.

The stored data can also be used to predict future health scores for a user. A prediction module can analyze past data (e.g., fitness habits, eating habits, etc.) to extrapolate a predicted health score based on an assumption that the user will continue to act in a predicable manner. For example, if the data shows that a user has exercised one hour every day for the past thirty days, the prediction module can predict, in accordance with a prediction algorithm, that the user will continue to exercise one hour for each of the next three days. Accordingly, the scoring module can calculate a predicted health score at the end of the next three days based on the information from the prediction module. It can also factor the prediction into other actions. For example, the system can suggest a more exerting physical activity level or challenge to someone who has a high health score but is predicted based on past experience to then take a number of days off for recuperation. Furthermore, the system can provide encouragement to the user to maintain a course of activity or modify behavior. For example, the system can send a message to the user indicating that if the user increased fitness activity by a certain amount of time, the health score would go up by a certain amount. This would allow the user set goals to improve health.

The use of the health score allows for a relative comparison of a user's health with that of another person's even though each person can have very different characteristics, which would make a direct comparison difficult. For example, a first user (User 1) can have a very different body composition or engage in very different fitness activities as compared to a second user (User 2), which makes direct comparison of the relative health of each user difficult. The use of the health score makes comparison of the two users possible with relative ease. In one example, User 1 is slightly overweight, which would tend to lower User 1's health score. However, User 1 also engages in large amounts of fitness activities, thereby raising the user's overall health score. In contrast, User 2 has an ideal body weight, which would contribute to a high health score, but engages in very little fitness activity, thereby lowering the health score. User 1 and User 2 are very different in terms of their health related parameters. Accordingly, it would be very difficult to assess and compare the relative health of User 1 and User 2. In accordance with the invention, information related to certain health parameters is collected from User 1 and User 2, which is used to calculate an overall health score. A comparison of User 1's and User 2's health score allows for an easy assessment and comparison of the health of these two users even though they are very different and have very different habits. Therefore, the health score has significant value so that members of a group can compare their relative health and so that other entities (e.g., employers, health care insurers) can assess the health of an individual. Examples are shown in FIGS. 3d and 3e in which tabular (current) and graphical (historic, current and predicted) scores of different users are shown. As can be seen in FIG. 3e, Katrin is expected to surpass the user (Andre) shortly unless he improves his lifestyle and performance. In FIG. 3d, the impact of the decay algorithm is illustrated to show the effect on the health score of a given user (Andre) and the people he has identified as friends. As noted, user Andre has a current health score of 669 which situates this user between friends Irene (health score 670) and Helle (health score 668). The decay algorithm has acted on all of the health scores shown in the screen shot of FIG. 3d, as indicated in the "Δ 1 Day" column. More particularly, most of the friends of Andre have had their health score reduced by 1 point due to the reason of "no activity." A lack of data input to the system is a basis for the processor executing the decay algorithm to determine a "no activity" status for a given user. The one day effect of this status according to the illustrated decay algorithm for most of the users is a reduction of 1 point in one day, and a reduction of 5 points over the course of a week. As such, the decay algorithm can have a tapering, non-linear impact on an overall health score.

As illustrated, user Andre has had moderate activity registered into a memory that is accessible to the system. As a result, the moderate activity is processed and results in a one day change (delta) that is positive, and a change that counteracts the influence of the decay algorithm. Consequently, Andre will be able to observe, as well as the friends that have access to his published health score, that he increased his score from 667 to 669 in one day, and from 662 to its present value over the past seven days as a result of "moderate activity." Moreover, a prediction is computed using the underlying algorithm and an extrapolation of data based on most recent reasons (that is, received data) to increase another 5 points. On the other hand, due to low activity, but a good diet, Helle in the same time period went down 1 point in the last day and a total of 1 point in the last 7 days and is predicted to lose another point if this rate continues. As such, Helle is provided with feedback by execution of the algorithm and the outputs provided by the system which can encourage more activity. On the other hand, Irene has no activity and a poor diet which results in a more aggressive change to her current health score and the longer-view historical and predicted impact on her score. Again, this feedback, which can be provided to users and their friends or to members of a group of users that have associated together for a challenge, etc. to provide individual or team motivation to engage in fitness activities, eat well, and so on.

Moreover, the health score provides an indication of the relative health of the individual without revealing the underlying data used to calculate the health score, which can be sensitive information. For example, a user may be uncomfortable revealing his or her weight, age, or amount of time they spend exercising to others persons or entities. Persons can be embarrassed to share his or her weight or the fact that they virtually never go to the gym. However, since the health score is derived from several factors, the underlying data used to calculate the score is kept private. This feature will facilitate the sharing of the user's overall health because users will not have to disclose private data about themselves. For example, a person may be slightly overweight, but she goes to the gym often. Accordingly, that person can receive a relatively good health score. While the person may not want to disclose her weight, she can still disclose her health score which conveys information about her relative health without disclosing the underlying details. The intrinsic medical parameters (e.g. weight, height, etc.) and the extrinsic physical activity parameters (e.g. exercise duration, frequency, intensity, etc.) are transformed into a masked composite numerical value. The masked numerical value is published while the collected information concerning the intrinsic medical parameters and extrinsic physical activity parameters is maintained private. The underlying intrinsic medical parameters and extrinsic physical activity parameters are protected so that a third party is not able to determine those parameters based on the health score number. This is because the parameters can vary in many different ways and yet the health score number could be the same (e.g., a heavier person that exercises frequently can have the same health score as a person that is not overweight but does not exercise as frequently). Thus, having the health score alone does not reveal a person's health related parameters. Accordingly, the underlying health statistics are masked, yet the health score can be used as a benchmark to indicate a person's health for a variety of applications.

After the scoring module calculates the health score of the user, at step 270, a publication module recalls from the memory the designated group of recipients that are authorized to receive the health score. The group of recipients can be friends or family of the user, sports teammates, employers, insurers, etc. At step 280, the publication module causes the health score to be published to the designated group. In the case that the information is to be published to a group of friends, the information can be published to a social networking internet based portal in which access to the data is limited to those designated members of the group.

The health parameter data and health scores can be stored over time, in a memory or other database, so that a user can track his or her progress. Charts can be generated in order for a user to track progress and analyze where there can be improvement in behavior. Moreover, trends can be identified that can lead to the diagnosis of medical problems and/or eating habits. For example, if a person's weight is continuing to increase despite the same or increased amount of fitness activity, the system can trigger or suggest that they seek certain medical tests (e.g. a thyroid test, pregnancy test) to determine the cause of the weight gain.

In certain implementations, the majority of the system is hosted remotely from the user and the user accesses the system via a local user interface device. For example the system can be internet based and the user interacts with a local user interface device (e.g., personal computer or mobile electronic device) that is connected to the internet (e.g., via a wire/wireless communication network) in order to communicate data with the internet based system. The user uses the local interface device to access the internet based system in which the memory and software modules are operating remotely and communicating over the internet with the local device. The local device is used to communicate data to the remote processor and memory, in which the data is remotely stored, processed, transformed into a health score, and then provided to the designated groups via a restricted access internet portal.

Alternatively, the system can be primarily implemented via a local device in which the data is locally stored, processed, and transformed into a health score, which is then communicated to a data sharing portal for remote publication to the designated groups.

The system can be implemented in the form of a social networking framework that is executed by software modules stored in memory and operating on processors. The system can be implemented as a separate, stand alone "health themed" social networking system or as an application that is integrated with an already existing social networking system (e.g., Facebook, MySpace, etc.). The user is provided with a homepage in which the user can enter information, manage which information is published to designated groups, and manage the membership of the designated groups. The homepage includes prompts to the user to enter the health related information for the each of the various parameters. The user can enter his or her weight, date of birth, height, fitness activity, and other health related information. The user's health score is then calculated. The health score is shared with other users that are designated as part of a group permitted to have access to that information. Moreover, the user can view the health score information of others in the group. Accordingly, the user is able to compare his or her overall health with the health of others in the group. Comparison of health scores with others in the group can provide motivation to the individuals in the group to compete to improve their health scores. Other information, such as health tips, medical news, drug information, local fitness events, health services, advertising and discounts for medical and/or fitness related supplies and service, issuance of fitness challenges or health related goals, for example, can be provided via the homepage.

In further implementations, the health score can be a composite of a Metric Health Model score and a Quality of Life Model score. Combining scores from multiple models provides a more holistic assessment of a user's health. The Metric Health Model score assesses a user's health based on relatively easily quantifiable parameters (e.g., age, sex, weight, etc.) and compares those numbers to acceptable populations study models. The Quality of Life Model score focus on a user's self-assessed quality of life measure based on responses to a questionnaire (i.e., the system takes into account the user's own assessment of their health and life quality) because there are correlations between how an individual "feels" about his or her life and a realistic measure of health. A combination of the scores from these two models, which will be discussed in more detail below, provides a more inclusive and holistic assessment of health.

The Metric Health Model score is based on medical parameter information of a user, such as their medical history information, attributes, physiological metrics, and lifestyle information to the system. For example, the system can provide the user a questionnaire to prompt responses (yes/no, multiple choice, numerical input, etc.) or provide the user with form fields to complete. Medical history information can include the user's history of medical conditions and/or the prevalence of medical conditions in the user's family Examples of medical history information can include information such as whether the user has diabetes, has direct family members with diabetes, whether the user or family members have a history of heart attack, angina, stroke, or Transient Ischemic Attack, a history of atrial fibrillation or irregular heartbeat, whether the user or family members have high blood pressure requiring treatment, whether the user or family members have hypothyroidism, rheumatoid arthritis, chronic kidney disease, liver failure, left ventricular hypertrophy, congestive heart failure, regular use of steroid tablets, etc.

The Metric Health Model score can also be based on user attributes. The attributes can include age, sex, ethnicity, height, weight, waist size, etc. In addition, Metric Health Model score can be based on physiological metrics of the user. Examples of physiological metrics can include systolic blood pressure, total serum cholesterol, high-density lipoprotein (HDL), low-density lipoprotein (LDL), triglycerides, high-sensitivity C-reactive protein, fasting blood glucose, etc. The inputs can also include parameters of a user's lifestyle. For example, lifestyle parameters can include inputs about whether the user is a smoker (ever smoked, currently smokes, level of smoking, etc.), how much exercise the user performs (frequency, intensity, type, etc.), type of diet (vegetarian, high-protein diet, low-fat diet, high-fiber diet, fast-food, restaurant, home cooking, processed and pre-packaged foods, size of meals, frequency of meals, etc.). These are some of the examples of parameters that can be used to compare the user's health indicators to survival probability models in order to calculate the user's Metric Health Model score.

Survival probability prediction models can be used to predict the probability that an individual will suffer one or more serious health events over a given time period. Mathematical models can estimate this probability from observed population characteristics. Using observational data on a set of unambiguous severe health events, such as stroke or cardiac infarction, models can generate the probability that an individual will suffer one such event over a given time horizon from a set of measurements of markers, or predictors, for the event (e.g., information about a user's medical history, attributes, physiological metrics, lifestyle, etc. as described above). The time distance between the moment the predictors are measured, and the target event that is generated by such models, is referred to as a survival probability, although it must be understood that not all target events considered are necessarily fatal.

These survival probability models are typically derived from the study of generally large populations that are followed for a considerable length of time, usually more than ten years, and the statistics collected on the observation of the target event(s) are summarized and generalized using mathematical methods. There are a number of such models that exist that have been extensively validated and maintained and improved by periodically updating the model's parameters using new data. Examples of existing models can include a subset of models developed and maintained by the Framingham Heart Study (an extensive bibliography on results obtained from the Framingham Heart study is available at www.framinghamheartstudy.org/biblio), a subset of the models developed and maintained by the University of Nottingham and the QResearch Organization (see, for example, J Hippisley-Cox et al, Predicting cardiovascular risk in England and Wales: prospective derivation and validation of QRISK2, BMJ 336: 1475 doi: 10.1136/bmj.39609.449676.25 (Published 23 Jun. 2008)), the ASSIGN model developed by the University of Dundee (see, for example, H Tunstall-Pedoe et al, Comparison of the prediction by 27 different factors of coronary heart disease and death in men and women of the Scottish heart health study: cohort study; BMJ 1998; 316:1881), the Reynolds model (see, for example, P M Ridker et al, C-Reactive Protein and Parental History Improve Global Cardiovascular Risk Prediction: The Reynolds Risk Score for Men, Circulation 2008; 118; 2243-2251, and Development and Validation of Improved Algorithms for the Assessment of Global Cardiovascular Risk in Women, JAMA, Feb. 14, 2007-Vol 297, No. 6), the PROCAM model from the Munster Heart Study (see, for example, Simple Scoring Scheme for Calculating the Risk of Acute Coronary Events Based on the 10-Year Follow-Up of the Prospective Cardiovascular Münster (PROCAM) Study, Circulation. 2002; 105:310-315), and the SCORE model (see, for example, R M Conroy et al, Estimation of ten-year risk of fatal cardiovascular disease in Europe: the SCORE project, European Heart Journal (2003) 24, 987-1003). Other constituent risk models can also be included. In addition, precursor models can also be used. Precursor models predict the development of a first condition (e.g. high blood pressure), wherein the development of the first condition is predictive of developing a second condition (e.g., heart disease). There are models that generate estimates of the probability of developing diabetes or high blood pressure, for example, which are two important predictors of mortality. A high probability of developing diabetes in five years, for instance, will independently increase the probability of a serious cardiovascular event within the next ten years. Several such precursor models can be included and the inclusion of precursor models leads to more accurate metric risk models, but more importantly, also leads to the possible reduction of the risk of mortality through well-defined modifiable aspects of lifestyle.

Traditional survival probability models have certain inherent limitations that result from the procedures used to build them. In deriving such models, researchers compromise between accuracy and usability. It is difficult for an inductive model, meaning a model derived directly from data, to include all possible predictors. This is in part because not all relevant predictors of a particular event are known, but also in part because some known predictors may be difficult or expensive to measure. In fact, several well-known markers of risk, such as genetic factors, are often not included in such models. Therefore, several potential and known predictive metrics can be excluded as covariates when deriving a given survival model.

Survival probability models are built using data collected from a given population, and thus summarize and generalize morbidity and mortality characteristics of the studied population. However, such a model might be at variance when compared with risk estimates derived from other populations. When a given model is used in a population that differs from the one where the model was built it often underestimates or overestimates a particular risk because only a few predictors are often considered, and because other relevant predictors that may not be included in the model might very well differ between two populations.

Given the above discussion, together with basic probabilistic logic, a judicious combination of models derived for several different populations will generate a better view of the risks that an individual picked at random is exposed to, and will thus be more robust in estimating risks for the population at large. Furthermore, based on mathematical grounds, under very general assumptions, certain model combination methods, referred to as predictor boosting, can improve the accuracy of the constituent models. In fact, boosting a set of models, when done correctly, will produce a model with accuracy that is, at worst, equal to that of the most accurate model in the boosted set.

Accordingly, the Metric Health Model score can be calculated by comparing the user's medical parameter information to the survival probability models. A score, preferably in the range of 0 to 1000, with the top end signifying perfect health and the low side signifying poor health, can be derived following a two-step process. First, an overall survival probability is obtained from a combination of the survival probabilities generated by individual survival probability models, as described above. Second, the resulting survival probability, which is a number in the 0 to 1 range, is transformed using a parametric nonlinear mapping function into the 0 to 1000 range. The parametric mapping function is tuned so that it is linear, with a high slope, in the region of typical survival probabilities, and asymptotically slopes off in the low and high ends of the survival probability distribution. The mapping function is designed to be strongly reactive to changes in the typical survival probability region.

As discussed above, the health score can be composed of the Metric Health Model score, and also the Quality of Life Model score. The Quality of Life Model score is based on a user's answers to a set of questionnaires. The system can include several different questionnaires with some questions in common. The type of questionnaires and the type of questions therein presented to the user can be tailored based on a user's health parameters (i.e., user age, other data in the user's medical history, etc.). A specific questionnaire can be generated and presented to the user on the basis of information on the user that is known to the system. The questions can be presented with an appropriate multiple choice response that the user can check/tick on a form, with no free-form text is entered by the user to permit easier assessment of the responses. Other types of responses are possible (e.g., rating how true a statement is to the user 1-10). The following list provides several sample questions (in no particular order) on a number of health-related quality of life topics that can be used in a system questionnaire.

Sample Questions:
How do you rate your quality of life?
How do you rate your overall health?
How much do you enjoy life?
To what extent do you feel your life to be meaningful?
How well are you able to concentrate?
How safe do you feel in your daily life?
How healthy is your physical environment?
Are you satisfied with your appearance?
To what extent do you have the opportunity for leisure activities?
How much do you need any medical treatment to function in your daily life?
For how long have your activities been limited because of your major impairment or health problem?
Do you need help in handling your personal care needs because of health problems?
Do you need help in handling your routine needs because of health problems?
Are you limited in any way in any activities because of any major impairment or health problem?
How true or false is each of the following statements for you?:
  I seem to get sick a little easier than other people
  I am as healthy as anybody I know
  I expect my health to get worse
  My health is excellent
Do you suffer from any of the following major impairment or health problem that limits your activities?:
  Arthritis or rheumatism
  Back or neck problem
  Cancer
  Depression, anxiety or any emotional problem
  Vision problem
  Fractures, bone/joint injury
  Hearing problem
  Breathing problem
  Walking problem
  Other impairment or problem
During the past 30 days, for about how many days:
  was your physical health not good?
  did pain make it hard for you to do your usual activities, such as self-care, work, or recreation?
  have you felt sad, blue or depressed?
  have you felt worried, tense or anxious?
  have you felt you did not get enough rest or sleep?
  have you felt very healthy and full of energy?
  have you been a very nervous person?
  have you felt so down in the dumps that nothing could cheer you up?
  have you felt calm and peaceful?
  did you have a lot of energy?
  have you felt downhearted and blue?
  did you feel worn out?
  have you been a happy person?
  did you feel tired?
How satisfied are you with:
  your sleep?
  your ability to perform your daily living activities?
  your capacity for work?
  yourself?
  your personal relationships?
  your sex life?
  the support you get from your friends?
  the conditions of your living place?
  your access to health services?
  your transport?
Are you limited in any of the following activities because of your health?:
  Vigorous activities, such as running, lifting heavy objects, participating in strenuous sports
  Moderate activities, such as moving a table, pushing a vacuum cleaner, bowling, or playing golf
  Lifting or carrying groceries
  Climbing several flights of stairs
  Climbing one flight of stairs
  Bending, kneeling or stooping
  Walking more than a mile
  Walking several blocks
  Walking one block
  Bathing or dressing yourself This list above is just a sample of questions that can be presented to a user. The user's responses to the questions are assigned a value. For example, each of the multiple choice responses can be assigned a particular value, and all of the user's response can be tallied to generate a score. In addition, different questions and different responses can be weighted differently since some questions, or the severity of the response, can have a greater predictor of the user's health. The system can also assign a value based on the user's response to a combination of questions, because certain combinations can be more predictive of health. Accordingly, by assessing the user's responses to the questionnaire a Quality of Life Model score can be derived. Preferably, the Quality of Life Model score is a numerical value in the range of 0 to 1000.

Figure 4A:
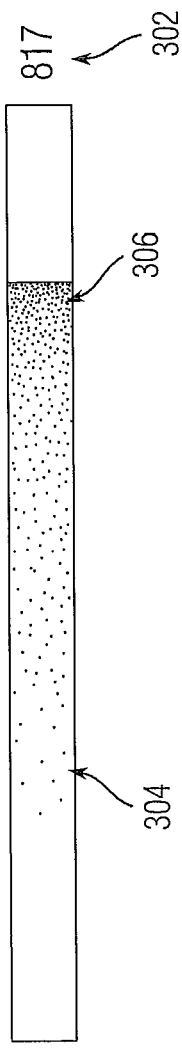
FIG. 4a is an illustration of a data presentation format according to one embodiment of the invention.

The health score is computed as a weighted average of the Metric Heath Model score and the Quality of Life Model score. The health score can presented to the user. The health score can be presented as a numerical value, as a graphic value (i.e. as a meter, bar, or slider), or a combination of the both, for example. Referring to FIG. 4A, the health score is presented 15 by a combination of a numerical score 302 and a slider 304. The slider can also be color-coded to indicate the score. The position of the slider bar 306 indicates the user's score.

One advantage of the presentation of the health score is that it is not necessary to present the survival probabilities and raw metrics to the user. Instead, users are presented with a standardized score. Preferably, this is true of the overall Metric Heath Model and Quality of Life scores, but it is also true of the relevant model inputs. This is done mainly to standardize all output, in the sense that users do not need to know whether high values of a particular input variable are good or bad; in all cases, high scores of any input value lead to higher overall health score values, and low input variable scores lead to lower overall values of the health score.

Figure 4B:
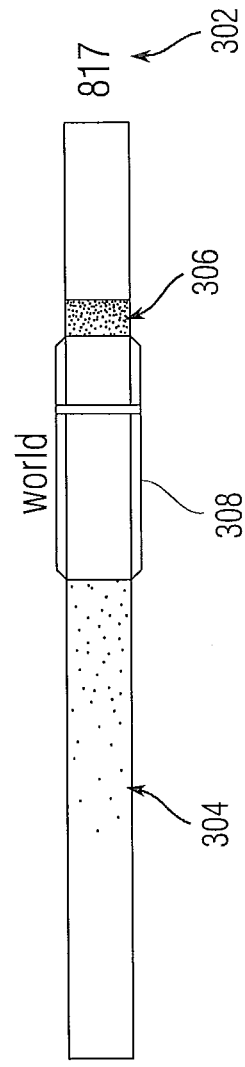
FIG. 4b is an illustration of a data presentation format according to one embodiment of the invention.
Figure 4C:
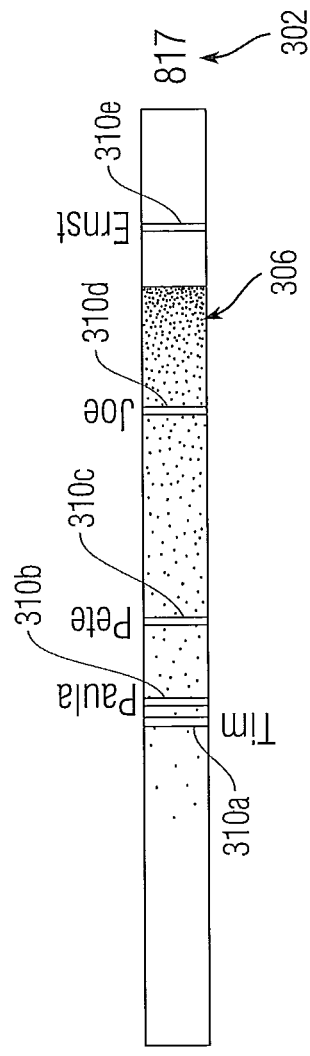
FIG. 4c is an illustration of a data presentation format according to one embodiment of the invention.
Figure 4D:
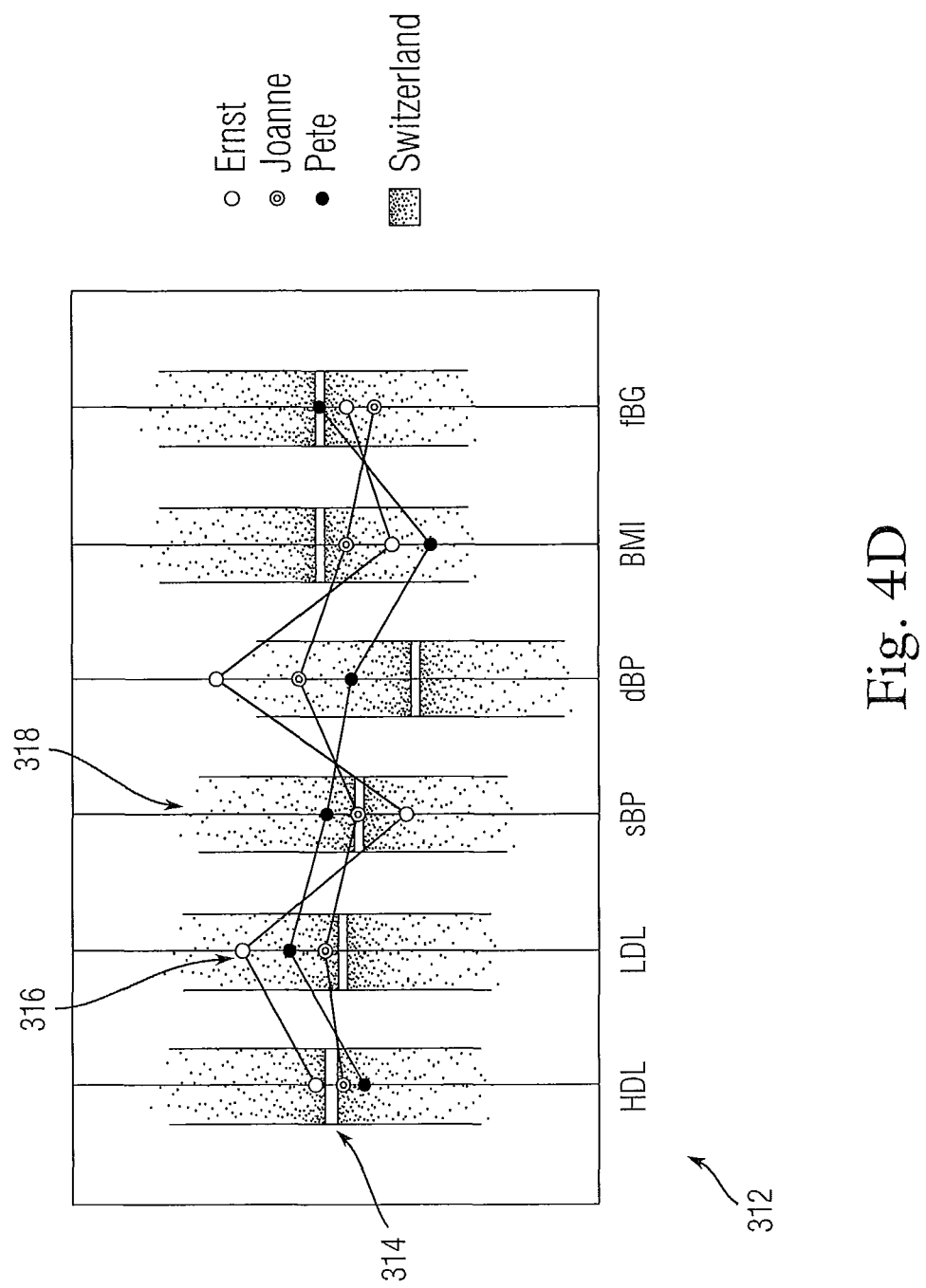
FIG. 4d is an illustration of a data presentation format according to one embodiment of the invention.

Furthermore, another advantage of the standardized health scores is that users can compare health scores against other users. This allows for comparative bench marking (against friends, co-workers, etc.) with other users. Such score comparisons can be a part of a game component of the system in which the user competes against other users, as will be described in more detail below. Gaming aspects of the system can be used motivate the user of the health score system, such as a comparison of scores among user-selected groups, comparison of individual scores within configurable subpopulation distributions, time-tracking of scores, and setting of goals, among others. Referring to FIG. 4B, the users numerical score 302 and graphical score 306 are presented in combination with a range of scores 308 from a group (e.g. the world) so that the user can see how his/her score compares to others in the group. The gaming incentives can be extended by users to allow the comparison of health scores between users that can differ substantially in one or more of several specific input parameters, such as age, weight, and prior risk conditions. The system highlights improvements in modifiable user metrics, particularly in lifestyle components, and these improvements in score provide user incentives. This allows fair competition between users of a father and his children, for example, via the health score. In one aspect, the health score provides equalization between users of different characteristics and is thus similar to that of a handicap in some sports. Referring to "FIG. 4C, the user's score 306 is compared to the scores 310a-e of a user selected group of friends. Referring to FIG. 4D, the user's individual medical parameters (e.g., the medical data provided as a part the Metric Health Model) can be compared against other users graphically without revealing the underlying actual values. The high-density lipoprotein (HDL) level, low-density lipoprotein (LDL) level, systolic blood pressure (sBP), diastolic blood pressure (dBP), body mass index (BMI), and fasting blood glucose (fBG) level are shown on a graph 312. The user's scores are represented by a line 314, the user's friends scores are each represented by a different dot 316, and a distribution block 318 for a larger population group (e.g., Switzerland) is also shown. Thus, the user can compare their individual parameters to a group of friends and the average for a large population group.

Users can input data into the system at the time of an event (i.e., exercise event, food consumption, blood pressure measurement, etc.), and see the resulting update of their health score in real-time. The system can include drill-down capabilities, allowing users to see the various health score component scores, including tracking over time and the corresponding trends in all scores; it also includes the setting of goals on the various scores.

As an example of use of the system, upon registration with the system (e.g., the initial use of the system), a user is prompted to provide medical history data. The user is also prompted to respond to a complete Quality of Life questionnaire selected by the system for the given user based on the medical history and user parameters supplied by the user. After the registration, at periodic intervals, users are presented with short subsets (3 to 5 questions) of their custom Quality of Life questionnaire to keep their responses up to date and track changes. Users can enter inputs for Metric Health Model at any time, and the system prompts the user for values that have not been updated for some time. Inputs to the Metric Health Model can be acquired automatically by the system by accessing a series of digital measuring devices that have been integrated into the system (e.g., the system can comprise a mobile electronic communication device, for example, a smart phone, that is in wireless communication with a measurement device, such as a blood glucose monitor, so that parameters can be measured, transmitted, and stored by the system). These can include weight, blood glucose, physical activity, and other parameters. Several or multifunction digital measurement devices can be included in the system. In the case of medical parameters that are more difficult to obtain with a home measuring device, such as serum lipid concentration levels, users are only prompted to provide the relevant data once per (system) configured time period (e.g., annually and coinciding with a user's routine physical medical examination).

To avoid false scores, the system can include several algorithms to assess the validity of user inputs. The validation methods can range from ones based on outlier detection to ones based on multidimensional likelihood estimators. When the system detects a possible bad input value it flags it and prompts the user to either confirm the value or to enter a new one.

The system can generate all its scores, even when missing one or more inputs. It does this by imputing the missing value or values using a variety of statistical methods that range from ones based on global population statistics, to methods based on the use of more complicated statistical models that are built into the platform. However, whenever inputs include imputed values, the system clearly flags all affected scores, and periodically alerts the user to provide the missing data. The system can also allow for score simulation, in which the user can temporarily adjust his or her parameters so that a user can see how changing certain parameters (e.g., losing weight) affects the user's score.

The system can also provide recommendations to the users to take certain actions that can improve the user's health score. These recommendations can be very specific when any input variable is in its danger zone, and more generic when any input variable is outside its optimal range.

As discussed above, the health score can be used as a part of a game or competition aspect of the system. The game aspect increases the fun element of the system for the user and increases the user's affinity to continue to use the system. The game aspect can come in the form of obtaining higher levels based on achievements, competing against others (e.g., in a league), and/or completing challenges. The "level" is an overall indication of progress. The level can be monotonically increasing and will increase by gaining activity points. Activity points can be gained from performing numerous activities, such as time spent performing fitness activities (e.g., exercising), improving one's health score, improving one's BMI, taking part in discussions on the system (e.g., the system can be a web-based social networking platform and discussions or "classes" can be offered to teach fitness skills). A user's level can be displayed on a user's profile and in discussion posts so that other users can see each other's level. A user's level status can also provide access to specific items, system features and functionality, or rewards (e.g., branded apparel).

Users can also compete within leagues in the system. The leagues are composed of groups of users and the users within the league can compete against each other (as part of a team or individually). The leagues can compete for a limited time (e.g., monthly) and the leagues can be designated based on the level of the users (using the level of the user as discussed above), the type of activity being performed in the league, and the geographic region of the users. For example, one particular league can be the "bronze" (level) "mountain biking" (sport) "Greater Zurich Area" (region) league and a user's success in this league is measured by the distance traveled and elevation climbed (measured quantity). Thus, bronze level users living in the Greater Zurich Area that are interested in mountain biking can compete in this league. Limiting the leagues to a particular region gives the users something to relate with and all the users can share in common, and further allows users to meet face to face (e.g., for group exercise events). One issue with one big international league is that such a league may seem anonymous, crowded and meaningless to some users (members competing against members residing on completely different continents with language barriers can inhibit group or team mentalities). Limiting leagues to particular level brackets equalizes the playing field for users of particular skill levels. Quantities to be measured to determine performance in the league can include distance (horizontal, vertical) and duration of fitness activity performed, for example. Users can also form teams within the leagues. Team leagues work in the same way as the leagues outlined above, however the ranking is based on the team's overall performance. Teams increase the communal aspect of participation in the activity. Teams can be fixed in size (e.g., 2, 3, 5, 10, etc. users).

Users can also be presented by the system with challenges to complete. The challenges can set forth a time period for completion of a goal. The goals of the challenge can be, for example, healthscore improvement (normalized), completion of sport-related activity parameters (e.g., total distance, total climbing, etc.), or completion of a sport-related activity within a specific period of time (e.g., complete six minute mile on a specific route). The challenge can be public and any user can participate, or limited to a group (e.g. friends, co-workers, social group, etc.) As an example, a particular public challenge can be an inline skating challenge in New York City for the route around the Central Park Loop measuring the time taken for completion. Public challenges can be generated automatically by the system or by system administrators. Group challenges can be issued by group members. Challenges provide strong appointment dynamics, encouraging users to commit to exercise. Challenges (typically) have a lower time commitment than leagues. Route selection can be automated with the community. In a first step, the community can publish routes on the system platform (e.g., a social networking type website); in a second step, the system selects popular routes (i.e. routes with high user activity) as weekly challenges. Route validation is done by GPS tracking. Challenges can be safety screened to prevent the promotion of unduly risky challenge activities, such mountain biking dangerous downhill routes.

The league and challenge systems provide opportunities to grant achievements. Achievement status indications can be collected and displayed on a user's profile. Achievements are much like a trophy, medal, or award provided to the user for completing challenges and/or succeeding in a league activity. Many different achievements are possible, such as related to the number of friends the user has on the system (community participation), achievements related to the time, intensity, and number of fitness activities engaged in (level of fitness participation), achievements related to specific sport activities (e.g., distance run), the frequency a user measures their parameters (e.g., weight) in order to keep the system up to date, the amount of weight lost, or the ability to maintain ones BMI, for example. The following list is an exemplary set of achievements and the activities required to earn the achievements:

Exemplary Achievement List:
Challenger: Take part in a public challenge.
Accomplished Challenger: Take part in 10 public challenges.
Champion: Win a challenge.
Multi-sport Champion: Win a public challenge in two different sports.
International Challenger: Take part in a public challenge in two different countries.
International Champion: Win a public challenge in two different countries.
World Wide Challenger: Take part in a public challenge on each continent.
World Wide Champion: Win a public challenge on each continent.

Other aspects of the challenge and league systems are that the systems can be tied to marketing opportunities. For example, marketers can sponsor prizes for the winners of a challenge. The prize can be related to the challenge (e.g., gift certificate to health food score for winner of weight loss challenge). In addition, challenge routes can be selected to direct users to certain areas to increase tourism or to begin/end at selected destinations (e.g., bike challenge begins in front of sports equipment store).

One advantage of the system is that it provides users and groups of users with benchmarking capabilities. It allows other groups, such as insurance carriers or employers, to assess the relative health of individuals in order to determine the health related risks of each individual. Accordingly, users can compare themselves against others in order to assess their comparative health level amongst a group of friends. Insurance carriers can use the health score information to set premiums for an individual or a group of individuals (e.g. employees of a company). In other implementations, health scores can be provided for a group based on the health scores of the individuals in the group. For example, a health score can be calculated for a company based on its employees so that an insurance carrier can set premiums based on the health score of the company compared to other companies. In further applications, the health score can be used for assessing the health of professional athletes to determine the athlete's real market value. Vast amounts of money and resources are invested in athletes at all levels in professional sports. A large component of the decision about investing in an athlete is based on the past performance of the athlete. Other factors can include past physical injury history and the athlete submitting to a physical exam before the deal is complete. The health score can be used as an indicator of the athlete's current health and used as a predictor of the athletes future performance. If the athlete's health score were low, this can indicate that the athlete is more prone to suffering an injury or that physical performance will diminish. Accordingly, the health score can form a basis for a decision on whether to invest in an athlete. The health scores could also be used as a predictor of the outcome of a particular game played between two teams. For example, the health scores of the individual team members can be aggregated in order to provide a team health score. A comparison of the team health scores can be indicative of the likely outcome of the game between the two teams (e.g., the team with highest health score may be more likely to win). Such information can be used in gaming contexts such as fantasy sports teams, or in order to set odds for sports betting. The health score could be used for club competitions (e.g., group health improvement competitions, advertising based on a person's health score, gaming, tv/internet, etc.

Thus, in a broad aspect, a method according to the invention can be understood as collecting health related information, processing the information into a health score, and publishing the health score is provided. A system for implementing the method can include a computer having a processor, memory, and code modules executing in the processor for the collection, processing, and publishing of the information. Information concerning a plurality of health related parameters of a user is collected, particularly, both intrinsic values concerning the measurable, medical parameters of at least one natural person, and the extrinsic values concerning the activities of each such person(s) such as the exercise performed, the type of job the person has and the amount of physical work associated with the job (e.g. sedentary, desk job versus active, manual labor intensive job) and/or the calories/food consumed. Weighting factors are applied to the health related parameter in order control the relative affect each parameter has on the user's calculated health score. The health score is computed using the processor by combining the weighted parameters in accordance with an algorithm. The health score is published to a designated group via a portal. In one implementation, the portal is an internet based information sharing forum.

As such, the invention can be characterized by the following points in a method for collecting and presenting health related data:

- collecting information concerning a plurality of health related parameters of a user;
- storing the collected information in a memory;
- storing weighting factors in the memory;
- processing the collected information by executing code in a processor that configures the processor to apply the weighting factors to the health related parameters;
- computing a health score using the processor by combining the weighted parameters in accordance with an algorithm; and
- providing the health score to a designated group via a portal.

The methods described herein have been described in connection with flow diagrams that facilitate a description of the principal processes; however, certain blocks can be invoked in an arbitrary order, such as when the events drive the program flow such as in an object-oriented program implementation. Accordingly, the flow diagrams are to be understood as example flows such that the blocks can be invoked in a different order than as illustrated.

While the invention has been described in connection with certain embodiments thereof, the invention is not limited to the described embodiments but rather is more broadly defined by the recitations in any claims that follow and equivalents thereof.

We claim:

1. A computer implemented method for processing private health related data into a masked numerical score suitable for publishing, comprising the steps of:
    receiving first data into a memory, wherein the first received data represents at least one intrinsic medical parameter and at least one extrinsic physical activity parameter of a user;
    storing the first received data in the memory;
    storing weighting factors in the memory;
    processing the first received data by executing code in a processor that configures the processor to:
        apply respective ones of the weighting factors to the at least one intrinsic medical parameter and the at least one extrinsic physical activity parameter, and
        apply a decay component to the processed at least one extrinsic physical activity parameter to reduce the relative weight of the processed at least one extrinsic physical activity parameter for a physical activity in dependence on at least one factor associated with the user;
    transforming, by executing additional code in the processor, the processed first received data into a masked composite numerical value by combining the weighted parameters in accordance with an algorithm;
    establishing an exercise program with an exercise machine on the basis of the processed first received data or the masked composite score;
    receiving second data representing at least one other extrinsic physical activity parameter regarding activity by the user of the exercise machine associated with the exercise program;
    processing the second received data by executing code in a processor that configures the processor to:
        apply at least one of the respective weighting factors to the at least one other extrinsic physical activity parameter; and
        apply a decay component to the processed at least one other extrinsic physical activity parameter to reduce the relative weight of the processed at least one other extrinsic physical activity parameter;
    transforming the processed second received data into an updated masked composite numerical value by combining the weighted parameters in accordance with an algorithm; and
    automatically publishing the updated masked composite numerical value to a designated group via a portal, using code executing in the processor and free of human intervention, while maintaining the at least one intrinsic medical parameter, the at least one extrinsic physical activity parameter and the at least one other extrinsic physical parameter private.

2. The method of claim 1, wherein the at least one factor associated with the user is an age or an age range of the user and the decay component reduces the relative weight of the processed at least one extrinsic physical activity parameter for a first user of a first age or age range differently than for a second user of a second age or age range.

3. The method of claim 1, further comprising the step of averaging the published masked composite numerical value of a group of users to determine a group composite numerical value using further code executing in the processor.

4. The method of claim 1, further comprising the steps of:
    receiving data into the memory representing at least one extrinsic lifestyle parameter of the user, wherein the step of processing the first received data further includes executing additional code in the processor that configures the processor to:
        apply respective ones of the weighting factors to the at least one extrinsic lifestyle parameter, and
        apply a decay component to reduce the relative weight of the at least one extrinsic lifestyle parameter in dependence on the at least one factor or at least one other factor associated with the user,
    wherein the step of transforming the processed first received data further includes executing code in the processor that configures the processor to combine the at least one processed intrinsic medical parameter, the at least one processed extrinsic physical activity parameter and the at least one processed extrinsic lifestyle parameter in accordance with the algorithm.

5. The method of claim 1, wherein the steps of processing, transforming and publishing are performed automatically upon receipt of any of the received data.

6. The method of claim 1, further comprising monitoring the composite numerical value and causing triggering of a feedback communication by executing code in the processor and without human intervention.

7. The method of claim 6, wherein the feedback communication is operative to provide an alert to the user to initiate a physical activity or change a scheduled physical activity.

8. The method of claim 6, wherein the feedback communication comprises an alert sent to a predetermined person.

9. The method of claim 6, wherein the step of monitoring comprises monitoring value over time and triggering an alert in dependence on change over time.

10. The method of claim 6, wherein the step of triggering a feedback communication comprises sending an electronic communication directed to the user including directions on changes to the user's physical activity and/or lifestyle for improving the masked composite numerical value.

11. The method of claim 6, further comprising calculating, by executing additional code in the processor, a predicative masked composite numerical value, which is indicative of a predicted future state based on past data, using the received data of the user in accordance with a predicative algorithm and causing triggering of a predictive feedback communication.

12. The method of claim 1, wherein the step of processing the received at least one extrinsic physical activity parameter includes:
obtaining a measure of calories expended in the physical activity into the memory; and
executing further code in the processor that configures the processor to:
transform the measured calories into a metabolic equivalent, MET, value by dividing by the user's body weight;
divide the MET value between a health pool and a bonus pool, wherein the bonus pool has a predetermined size and any divided MET value exceeding the bonus pool size is allocated to the health pool; and
apply a daily decay component to the bonus pool;
wherein the step of transforming the processed first data comprises combining the processed at least one intrinsic medical parameter and a weighted health pool value in accordance with the algorithm.

13. A health monitoring system comprising:
a communication unit operable to receive first data on at least one intrinsic medical parameter and at least one extrinsic physical activity parameter of a user;
a memory arranged to store the first received data and to store weighting factors;
a processor arranged to process the first received data by executing code that configures the processor to:
apply respective ones of the weighting factors to the at least one intrinsic medical parameter and the at least one extrinsic physical activity parameter,
apply a decay component arranged to reduce the relative weight of the processed at least one physical activity parameter for a physical activity in dependence on at least one factor associated with the user;
the processor being further arranged to execute additional code to:
transform the processed first received data into a masked composite numerical value using the processor by combining the weighted parameters in accordance with an algorithm;
establish an exercise program with an exercise machine on the basis of the processed first received data or the masked composite score;
the communication unit further operable to receive second data representing at least one other extrinsic physical activity parameter regarding activity by the user of the exercise machine associated with the exercise program;
the processor being further arranged to process the second received data by executing additional code that configures the processor to:
apply at least one of the respective weighting factors to the at least one other extrinsic physical activity parameter and apply a decay component to the processed at least one other extrinsic physical activity parameter to reduce the relative weight of the processed at least one other extrinsic physical activity parameter; and
transform the processed second received data into an updated masked composite numerical value by combining the weighted parameters in accordance with an algorithm; and
a portal arranged to publish the updated masked composite numerical value to a designated group while maintaining the at least one intrinsic medical parameter and the at least one extrinsic physical activity parameter private.

14. The system of claim 13, wherein the at least one factor associated with the user is an age or an age range of the user and the decay component reduces the relative weight of the processed at least one extrinsic physical activity parameter for a first user of a first age or age range differently than for a second user of a second age or age range.

15. The system of claim 13, wherein the communication unit is further arranged to receive third data on at least one extrinsic lifestyle parameter of a user, wherein the processor is further arranged to process the third received data by executing additional code that configures the processor to:
apply respective ones of the weighting factors to the at least one extrinsic lifestyle parameter,
apply a decay component to reduce the relative weight of the at least one extrinsic lifestyle parameter in dependence on the at least one factor or at least one other factor associated with the user, and
transform the processed third received data by combining the at least one processed intrinsic medical parameter, the at least one extrinsic physical activity parameter and the at least one extrinsic lifestyle parameter in accordance with an algorithm.

16. The system of claim 13, wherein the processor is arranged to automatically perform the processing upon receipt of any of the received data.

17. The system of claim 16, further comprising a remote user device, the system being arranged to communicate with the remote user device during physical activity to receive at least selected ones of the at least one extrinsic physical activity parameter.

18. The system of claim 13, further comprising a monitoring unit arranged to monitor the composite numerical values and being arranged to cause triggering of a feedback communication upon detecting a predetermined event associated with the monitored composite numerical values.

19. The system of claim 18, wherein the feedback communication is operative to re-configure a program to define a scheduled physical activity for the user.

20. The system of claim 18, wherein the monitoring unit is arranged to cause transmission of an electronic communication directed to the user including directions on changes to the user's physical activity and/or lifestyle for improving the masked composite numerical value.

21. The system of claim 18, wherein the processor is further arranged to execute code that configures the processor to calculate a predicative masked composite numerical value that is indicative of a predicted future state based on past data, using the first received data of the user in accordance with a predicative algorithm and wherein the monitor is arranged to cause triggering of a predictive feedback communication.

22. The system of claim 13, wherein the processor is arranged to process the received at least one extrinsic physical activity parameter by executing code that configures the processor to perform steps including:

obtaining a measure of calories expended in physical activity;

transforming the measured calories into a metabolic equivalent, MET, value by dividing by the user's body weight;

dividing the MET value between a health pool and a bonus pool, wherein the bonus pool has a predetermined size and any divided MET value exceeding the bonus pool size is allocated to the health pool;

applying a daily decay component to the bonus pool; and transforming the processed first received data by combining the processed at least one intrinsic medical parameter and a weighted health pool value in accordance with the algorithm.

* * * * *